(12) United States Patent
de Guzman et al.

(10) Patent No.: US 7,919,330 B2
(45) Date of Patent: Apr. 5, 2011

(54) METHOD OF IMPROVING SENSOR DETECTION OF TARGET MOLCULES IN A SAMPLE WITHIN A FLUIDIC SYSTEM

(75) Inventors: Peter Patrick de Guzman, Orange, CA (US); Wayne Po-Wen Liu, Los Angeles, CA (US); Uichong Brandon Yi, Los Angeles, CA (US); Chang-Jin Kim, Beverly Hills, CA (US)

(73) Assignee: Advanced Liquid Logic, Inc., Research Triangle Park, NC (US)

( * ) Notice: Subject to any disclaimer, the term of this patent is extended or adjusted under 35 U.S.C. 154(b) by 596 days.

(21) Appl. No.: 11/917,655

(22) PCT Filed: Jun. 15, 2006

(86) PCT No.: PCT/US2006/023459
§ 371 (c)(1),
(2), (4) Date: Dec. 14, 2007

(87) PCT Pub. No.: WO2006/138543
PCT Pub. Date: Dec. 28, 2006

(65) Prior Publication Data
US 2009/0042319 A1    Feb. 12, 2009

Related U.S. Application Data

(60) Provisional application No. 60/691,073, filed on Jun. 16, 2005.

(51) Int. Cl.
*G01N 33/558* (2006.01)

(52) U.S. Cl. .......................................... 436/514; 436/174
(58) Field of Classification Search .................. None
See application file for complete search history.

(56) References Cited

U.S. PATENT DOCUMENTS

| | | | | |
|---|---|---|---|---|
| 6,057,149 | A * | 5/2000 | Burns et al. | 435/287.2 |
| 6,130,098 | A * | 10/2000 | Handique et al. | 436/180 |
| 6,150,180 | A * | 11/2000 | Parce et al. | 506/7 |
| 6,323,042 | B1 * | 11/2001 | Narang et al. | 436/514 |
| 6,361,958 | B1 * | 3/2002 | Shieh et al. | 435/7.1 |
| 6,524,456 | B1 * | 2/2003 | Ramsey et al. | 204/450 |
| 6,911,132 | B2 * | 6/2005 | Pamula et al. | 204/600 |
| 2004/0055891 | A1 * | 3/2004 | Pamula et al. | 205/98 |
| 2005/0037507 | A1 | 2/2005 | Gauer | |
| 2006/0039823 | A1 | 2/2006 | Yamakawa et al. | |

FOREIGN PATENT DOCUMENTS

| WO | 9954730 A1 | 10/1999 |
|---|---|---|
| WO | 03045556 A2 | 6/2003 |
| WO | 2006003292 A1 | 1/2006 |

* cited by examiner

*Primary Examiner* — Christopher L Chin
(74) *Attorney, Agent, or Firm* — William A. Barrett; Ward and Smith, P.A.

(57) ABSTRACT

Methods of improving microfluidic assays are disclosed. Assays can be improved (better signal to noise ratio) by using sessile drop evaporation as an analyte concentration step (enhanced signal) and repeated passes of wash droplets as a means to reduce non-specific binding (noise reduction). In addition multiple massively parallel analyses improve the statistical precision of the analyses.

20 Claims, 4 Drawing Sheets

METHOD OF IMPROVING SENSOR DETECTION OF TARGET MOLCULES IN A SAMPLE WITHIN A FLUIDIC SYSTEM

CROSS-REFERENCE TO PRIOR APPLICATIONS

The present applications claims the benefit of U.S. Provisional Application 60/691,073 filed on Jun. 16, 2005; the contents of which are incorporated by reference to the extent permitted by law.

GRANT INFORMATION

This invention was made with government support under DMI-0320082 awarded by the National Science Foundation. The government has certain rights in the invention.

BACKGROUND OF THE INVENTION

1. Area of the Art

The present invention concerns the art of microfluidics—namely the transporting and processing of microliter—volume fluid samples. More specifically, this invention addresses the problem of improving biosensor detection by processing the sample volume in the form of discrete mobile droplets which can then be agitated, evaporated or driven over one sensor or a plurality of sensors.

2. Description of the Prior Art

A key performance criterion of many biosensors is their ability to detect low concentrations of target biomolecules (by biomolecules we mean proteins, nucleic acids, polysaccharides, lipids and other organic molecules typical of living organisms; in some cases the target consists of small particles—e.g. cellular organelles or fractions—instead of individual biomolecules). This task is made more difficult because 1) the specific target biomolecules are almost always randomly distributed throughout the sample volume and not concentrated at the sensing site; 2) the presence of other non-target or non-specific molecules within the sample can degrade the sensor response, leading to either false positives or to masking target biomolecule detection in by background noise; and 3) the actual detection of captured target molecules may require application of secondary markers and/or reaction substrates to the sensor.

Rather than relying solely on random diffusion effects to bring the target molecules into proximity to the sensor, a variety of sample processing tactics have been employed to improve biosensor detection. These techniques include: 1) concentrating or focusing target molecules at the sensing site(s); 2) circulating, or agitating the sample volume at the sensing site(s); and 3) providing reaction substrates or other materials which enable or amplify detection. These methods are currently used in biosensor, lab-on-chip, micro-total-analysis, microarray and other microfluidic applications; however each of these techniques has its own drawbacks.

Focusing or concentrating target molecules within the sample volume via electrophoretic or other affinity means can also concentrate interfering non-target molecules which are attracted by the same effects intended to concentrate the target molecules. Therefore, a way to wash the sensor site, typically achieved by valving and pumping, must also be included to remove such non-target molecules. Generally, the target molecules will interact with the sensing site and resist removal by washing. Concentration can also fail when some or all of the target molecules are not sufficiently charged to be concentrated by electrophoresis and/or lack characteristics to be concentrated by the affinity method employed.

Rather than focusing by means of electrophoresis or otherwise concentrating target molecules from within the sample volume, some techniques seek to improve the probability of detection by circulating or agitating the entire sample volume over the sensing site. Circulation and agitation effects not only bring new target molecules into contact with the sensing site, but also serve to wash or remove non-target molecules from the site. However, to circulate or agitate the entire sample volume, cumbersome seals, valving and costly mechanical, pneumatic, or surface acoustic wave methods are typically required. Such complexity would likely impede application of such techniques to systems including numerous and/or highly distributed biosensors.

Once the target molecules have been captured by the sensing site, it is often necessary to treat the captured target molecules at the sensing site with a labeling or reaction solution to enable detection, amplify detection, and/or quantify the captured target molecules. For example, an antibody that has been fluorescently labeled and which is specific to the target molecule can be introduced to the sensing site to create an optical signature proportional to the number of captured target molecules. For some electronic sensors, a substrate solution that specifically reacts with the captured target molecule (or enzymes linked to the target molecule) thereby releasing molecules directly detectable by the sensor can be introduced to create an electronic signal that is proportional to the number of captured target molecules. However in either case, when the indicator or marker signal changes with time, precise timing is required in the delivery of the reaction solution(s) to achieve accurate comparisons. Unfortunately, leaky valving, air bubbles in channels, variations in capillary wetting characteristics and even differences in manual loading of samples and reagents often compromise precision timing of microfluidic delivery of such reaction solution(s).

DESCRIPTION OF THE INVENTION

The present invention solves these and related problems by circulating the entire sample over the sensing site not as a continuous stream, but rather as a series of discrete, moving droplets which can be exposed, agitated, or even concentrated through evaporation at the sensor in a repeated and well-defined and repeatable manner (timing of delivery and exposure, frequency of agitation, degree of evaporation, number of repeat passes, periodic washing, etc). Such a discrete series of moving droplets can be achieved by using a variety of mechanical, electronic, chemical, optical or other droplet handling methods. One example of such on-chip discrete droplet control is the microfluidic handling capability achieved via Electro-Wetting-On-Dielectric (EWOD) effects [see 1) J. Lee, H. Moon, J. Fowler, T. Schoelihammer and C.-J. Kim, "Electrowetting and Electrowetting-On-Dielectric for Microscale Liquid Handling", Sensors and Actuators, Vol. A95, 2002, pp. 259-268 and 2) S.-K. Cho, H. Moon and C.-J.

Kim, "Creating, Transporting, Cutting, and Merging Liquid Droplets by Electrowetting-Based Actuation for Digital Microfluidic Circuits", Journal of Microelectromechanical Systems, Vol 12, 2003, pp. 70-80 for background on EWOD].

Figure 1:
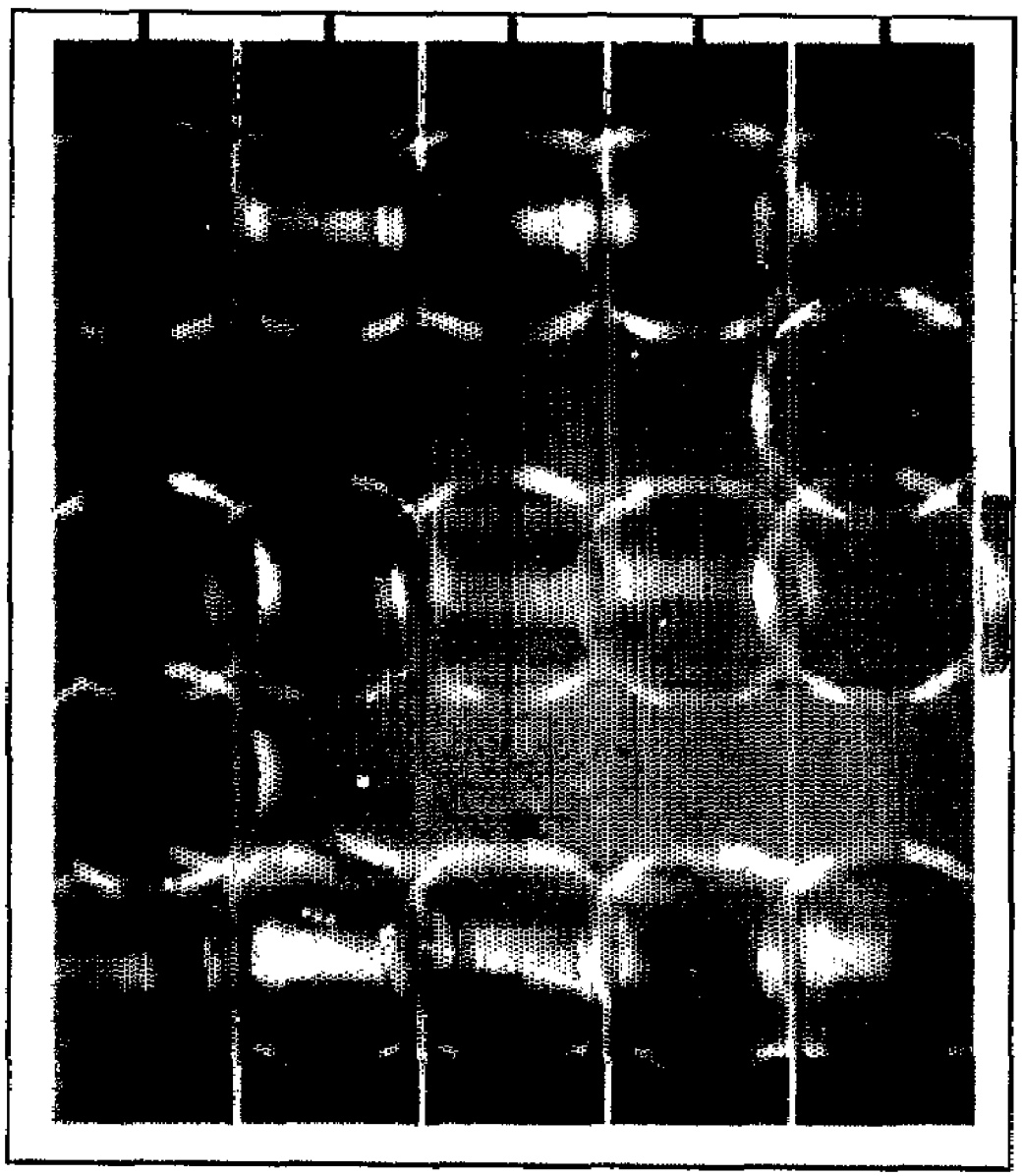
FIG. 1 shows a photograph of a single capillary droplet traveling along a preprogrammed path on a 5/5 array of EWOD electrode pads

FIG. 1 demonstrates the power and flexibility of EWOD: a single water droplet is traveling in a programmed "2" pattern on a 5×5 array of electrode pads. EWOD is ideal for driving sample droplets (containing target biomolecules and particles) because low voltages (10-20 volts) are effective and droplet travel paths and velocities are precisely controlled, pad by pad. In contrast to some methods, EWOD effects do not expose the target molecules to temperature extremes and/ or acoustic energy levels which can damage (i.e., denature) proteins, DNA and other biomolecules of interest. Further, the flexibility of EWOD configurations can enable disposable biosensor chips that are linked in highly distributed networks.

By parsing the sample volume into a series of discrete droplets wherein each droplet can be individually controlled, sample circulation and agitation can be applied locally over each sensor site rather than globally and in complete serial fashion to assure almost total exposure of the sample volume to each individual sensing site. That is, by making each droplet comparable in size to the sensing site and by transporting each droplet to interact with each sensing site in a controlled manner, diffusion path limitations on target molecules can be essentially eliminated. Conducting sample circulation/agitation and sensor washing in this manner also eliminates the cumbersome watertight seals, valving, or mechanical, pneumatic or surface acoustic methods which are often required where the entire sample volume is moved as a stream.

A highly local and powerful agitation effect can be achieved by driving each individual droplet over the sensor in one or a plurality of directions, at high speeds (~250 mm/sec) or with various cycles and combinations of dynamic motion, static rest and forced environmental effects. For example, one can program agitation effects to include a droplet being held stationary over the sensor for a given time TS, and then alternated with transport over the sensor at various velocities V, or combined other periodic dynamic and static rest effects. These highly localized agitation effects will bring particles in free suspension or molecules dissolved within the droplet and/or residing on the liquid/air and liquid/surface interfaces of the droplet in closer proximity to the sensor more effectively than methods which rely on global or whole sample agitation, circulation, and perturbation effects.

Driving or agitating one or more sample droplets containing target molecules over a sensor site also serves to mitigate unwanted adsorption of non-target molecules at the sensor site. Because the sensor site is typically treated to show or fabricated with some target-specific affinity properties, dynamic translation of a sample droplet will clear the non-target particles which have little affinity for the sensing site. This washing step can also be performed with a clean (i.e., non-sample) wash droplet. Thus separate wash steps or microfluidic mechanisms needed to achieve a separate washing effect can be eliminated by interleaving wash droplets into a series of sample droplets. In addition to simple washing, a series of "regeneration" droplets can be similarly moved over the sensor following analysis to strip all bound molecules from the sensor thereby readying the sensor for the next analysis.

Figure 2:
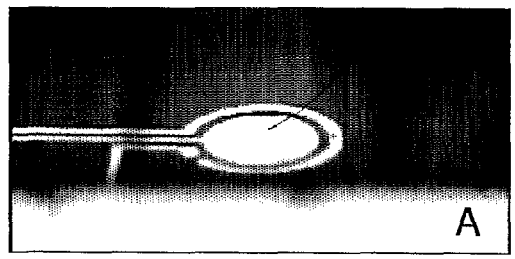
FIGS. 2A-2H shows a series of photographs illustrating the formation of a sessile droplet on a sensor surface and its evaporation over a period of 85 seconds.
Figure 2:
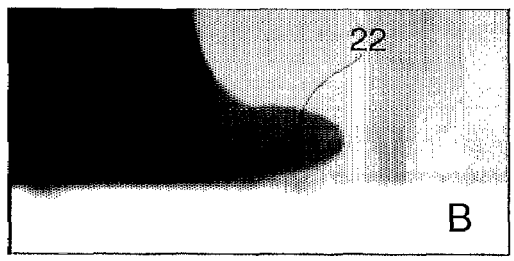
Figure 2:
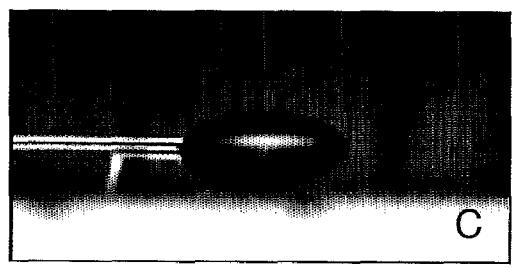
Figure 2:
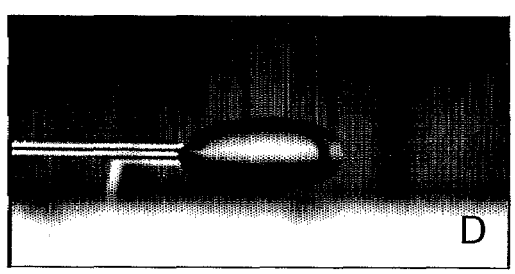
Figure 2:
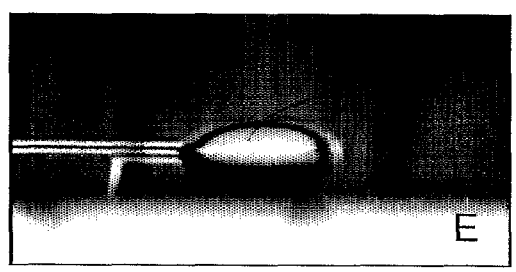
Figure 2:
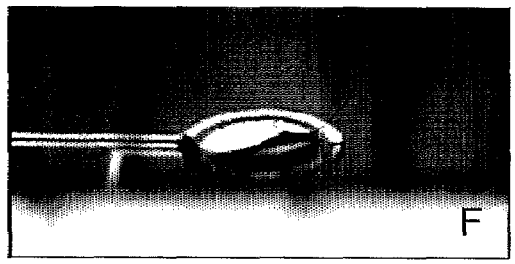
Figure 2:
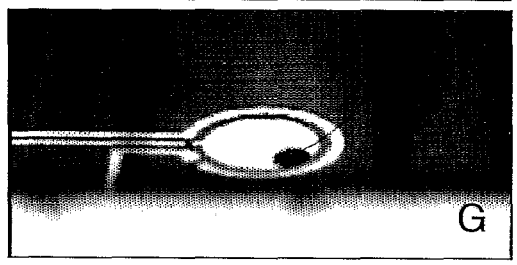
Figure 2:
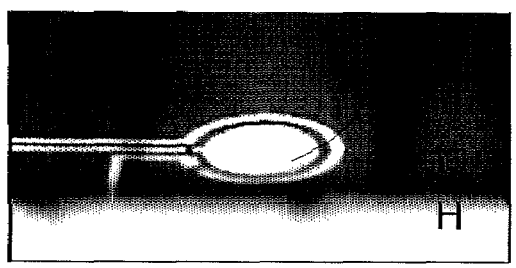

The ability to drive discrete droplets rather than continuous sample volumes also yields another unique benefit: as each sensing site is wetted by a passing droplet, a fixed sessile droplet is left behind on the sensor as is shown in FIG. 2. By "sessile" we mean a thin, residual volume of fluid that clings to the sensing surface after the main droplet has moved on. Sample concentration is then achieved as evaporation occurs and the surface of the sessile droplet recedes towards sensor surface, thereby moving target molecules into closer association with the sensor. A new sessile droplet is formed and refreshed with new target molecules by each passing sample droplet.

FIG. 2A shows a sensor surface 20 before the arrival of a sample droplet. FIG. 2B shows the passing (from right to left) of a sample droplet 22 over the sensor. In FIG. 2C the main sample droplet 22 has moved away leaving a sessile droplet 24 on the sensor surface 20. FIGS. 2D-2H shows the evaporation of the sessile droplet over a period of about 85 seconds. In FIG. 2H the sessile droplet 22 has completely evaporated.

Evaporation of a sessile droplet on a sensor can accelerate and amplify signal detection by placing the target molecules into close range with the sensor thereby achieving diffusion distances that are a fraction of the sensor diameter and/or forcing the target molecules into direct contact with the sensor. Furthermore, the sensor site is refreshed with new target particles with each pass of a sample droplet and subsequent formation of a new sessile droplet; sessile droplets can be quickly evaporated due to their high surface-to-volume ratio. By defining the time before the next mobile sample droplet is driven over the sensing site, the fixed sessile droplet can be evaporated in a highly controlled manner through natural or forced (e.g., elevated temperature and/or circulation of gas over the site) means for complete or partial evaporation.

Passing or agitating a follow-on sample droplet or a "wash" droplet (or a series of wash droplets) over the sensing site can then remove non-target molecules that have been adsorbed onto the sensor during the initial sessile droplet evaporation. The "wash" droplet can then be driven off the sensor and into a waste container before the next sample droplet arrives to add more target molecules to the sensor site.

The ability to program droplet driving can also enable direct, precisely timed and high speed transport (~250 mm/sec) of a reaction solution droplet over the sensor to aid or enable detection of successful target capture. This unique capability to control within a microsecond time scale the movement and mixing of droplets can 1) assure a near simultaneous conduct of parallel reactions (e.g., sample versus reference) used to evaluate specific target signal versus background or noise signal levels and 2) achieve highly repeatable enzymatic or other time based reactions which determine biosensor signal output. Thus, programmable droplet driving can be seen to enable high speed and precision sequencing of sample, wash and reaction solutions without application-or protocol-specific designs in channels, valving, pumps and chip layouts. This, of course, greatly increases the simplicity and flexibility of instrument design.

Figure 3:
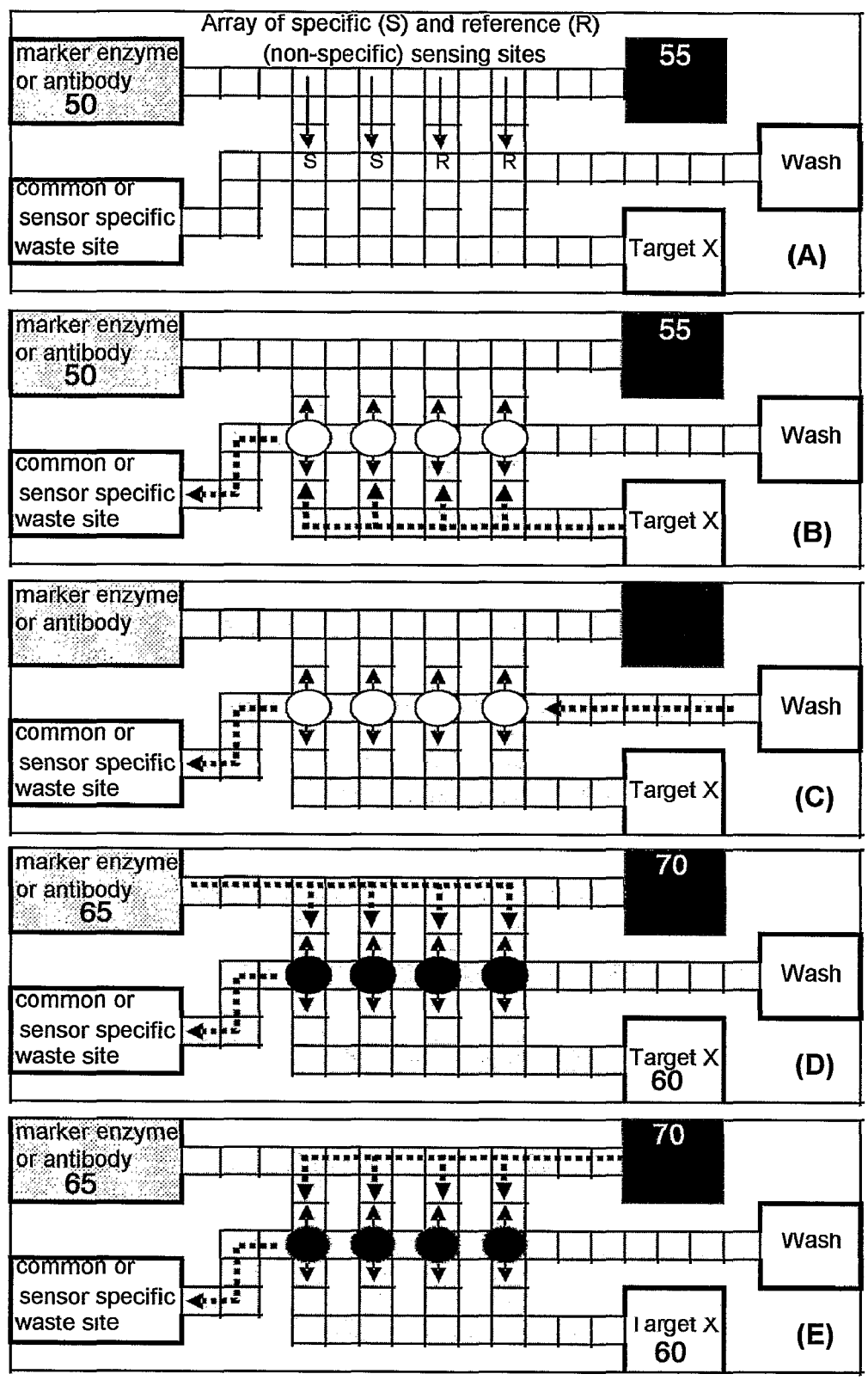
FIGS. 3A-3E is a series of diagrams showing precision parallel sample processing.

FIG. 3 demonstrates the abilities of the present invention to enable parallel processing. The diagrammatically illustrated assay is on a sensor site that is designed to bind, for example, a marker antibody (other specific binding molecules such as lectins or enzymes can, of course, be used). In this type of assay the specific binding molecules are allowed to attach to the sensor site. Then a test or analyte droplet is allowed to react with the sensor surface. If the test solution contains any target molecules (Target X), these molecules will bind to the antibody on the sensor surface. Finally, a second detection antibody that also binds to the target molecule is allowed to interact with the sensor surface. If target molecules are present on the surface, the detection antibody will bind enabling a detection signal that will be proportional to the number of target molecules. This type of "sandwich" assay is well-known to one of skill in the art. It will be appreciated that competitive and other assay formats can also be enabled by the inventive technology.

FIG. 3A diagrammatically represents a system with multiple sensor areas which may represent an array of specific (S) and reference (R)(non-specific) antibody coated sensor sites for detection of a target molecule. Droplets can be driven to these sensor sites over a path, circuit, network or array of EWOD driving pads from a number of different source reservoirs or distribution channels (for example, target or analyte solution, wash solution, target specific enzymes or antibody markers, reagents, etc.). The sensor sites are coated with various antibodies or other binding molecules. Here the droplets to coat the S pads come from the marker antibody reservoir 50 while the droplets for coating the R pads comes from the reagent reservoir 55 which contains a non-specific antibody. For sake of simplicity only one physical set of reservoirs is shown in the diagrams. In an actual set up multiple sets of reservoirs could be present. In the figures changes in the reference numbers indicate that different reservoirs are used in different phases of the process.

In FIG. 3B a series of droplets is generated from the target solution reservoir 60 and driven to and agitated (indicated by the double arrows) over a plurality of sensing sites to allow binding of any target molecules to the antibodies of the antibody-coated sensor surface. It will be appreciated that the reservoir 60 contains the test sample containing the analyte. After reacting with the surface, the target droplets are driven to waste (individual or sensor specific waste sites can be used in place of the common waste site shown here to prevent cross contamination, precipitation or similar reactions which may cause difficulties).

In FIG. 3C wash droplets are driven to and agitated over the sensor surfaces to remove non-target and unbound target molecules. These wash droplets are also driven to waste after the repeated agitation over the sensor surface. Finally, in FIG. 3D each of the sensors receives a droplet of a detection marker antibody, reagent or enzyme from a reservoir 65 that is designed to react with or bind to target molecules bound to the sensor surface. FIG. 3E illustrates a further variation where a subsequent series of reagent droplets can also be generated from reservoir 70 to react with any marker antibodies or enzymes that have attached to the bound target molecules. FIG. 3E is a situation where the detection antibody or reagent requires a second component to create the detection signal.

Parallel readings can be taken after: 1) the sensor sites have been exposed to target-specific reagents, antibodies or enzymes (FIG. 3D) or 2) after reagent droplets have been allowed to react with the bound target molecules. It will be appreciated that the readings can be by means of optical methods, electrochemical methods or other methods known to those of skill in the art. By making parallel readings as in 1) and 2) a control or blank reagent reading can be produced. It will be appreciated that the system readily allows for various components to be omitted to automatically create a series of internal controls and tests. Such flexibility is not possible with many alternative systems.

The reference sensing sites provide for measuring non-specific binding to the sensor surface thus yielding a background signal for the test solution. Comparing the S sensors with the R sensors gives a measure of non-specific binding of a particular reagent set (as a quality control for the reagents) as well as indicating the presence of interfering substance in the target solution. That is, the S sensing sites have a natural affinity for the target molecules and should capture more of these molecules than the R sites. An interfering substance might cause abnormal binding of the detection antibody to the R sensor sites. Parallel readings taken among the numerous capture sites will provide a ratio of specific versus non-specific signals (SNR or signal-to-noise ratio) that is proportional to the number of target molecules present.

In carrying out the process illustrated in FIG. 3 precision timing of droplet mixing enables simultaneous performance of: 1) a plurality of identical reactions to improve statistical confidence levels; 2) a plurality of evaluations of specific versus non-specific interactions with each evaluation containing numerous repeat reactions to reduce statistical uncertainty; and 3) multiple and uniformly timed analyte exposures and washings to take place over each sensor site to reduce statistical uncertainty and increase the SNR.

By achieving automated and precisely timed droplet manipulation at the chip level, far more repeatable and abundant data can be obtained as compared to manual pipette-based sample and reagent loading methods which are prone to human errors. Further, these results and can be obtained at far less cost and with greater flexibility than robotically driven pipette loading methods which require standardized plate dimensions and loading points.

EXPERIMENTAL RESULTS

Sample Concentration via Droplet Driving and Evaporation

Figure 4:
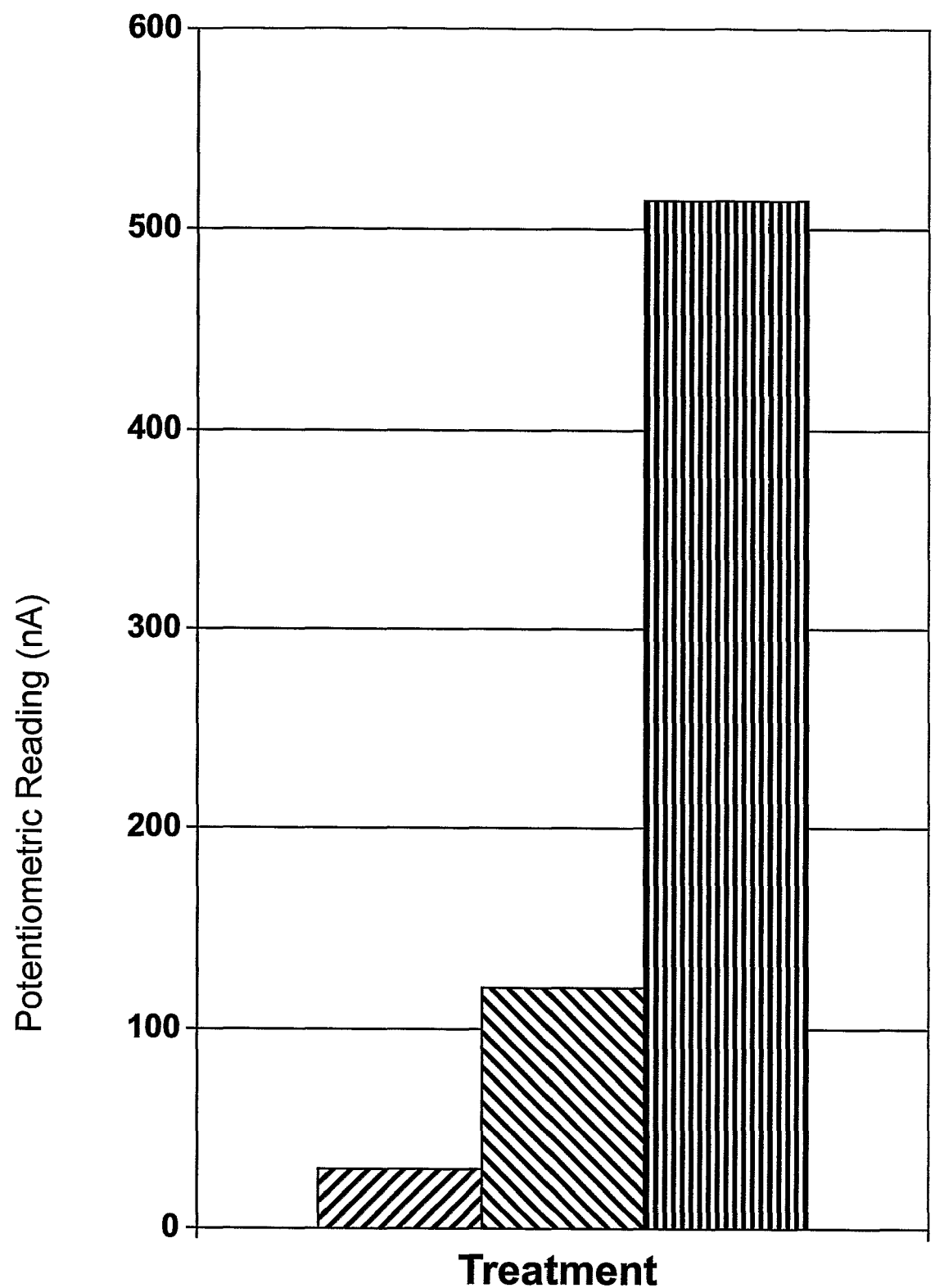
FIG. 4 is a chart illustrating the improved signal resulting from sample concentration.

FIG. 4 compares the results achieved with conventional and sample concentration methods achieved via droplet driving and evaporation. Baseline measurements (first column on left in figure) consisted of exposing a 1 mm diameter sensor for 10 min to a 5 mm diameter droplet containing Horse Radish Peroxidase (HRP) as a sample molecule. Following the 10 min period the HRP droplet was driven off the sensor and replaced by a reaction droplet containing a substrate. A resulting signal level of 30 nano-Amps (nA) was achieved. This method is analogous to conventional methods where a continuous sample volume, which is much larger than the sensing site, is held at rest over the sensor site for 10 minutes to allow for immune-capture via diffusion, and then a reaction solution is mixed in to achieve a detectable signal.

Two different sample concentration approaches were tested. The first sample concentration approach (second column from left in figure) consisted of driving an HRP droplet over the sensor to create a fixed sessile droplet, which was allowed to evaporate partially for one minute, before an additional pass of the HRP droplet was made over the sensor. After a total of ten droplet passes and ten partial evaporation periods (10 minutes total), a substrate-containing reaction droplet was driven to cover the sensing site and a resulting signal level of 120 nA was achieved giving a signal amplification of 4×. The second approach (third column from left in figure) consisted of repeating the sessile droplet method but allowing full evaporation between each of the 10 passes. This approach required 20 min and achieved a signal level of over 500 nA for a 16× signal amplification. That is, the time was doubled but the signal strength was squared.

Sample Washing via Droplet Driving

Washing is a critical portion of many assays because it clears non-specific molecules such as unbound antigens and unhybridized nucleic acid polymers from the sensor. We compared the washing effectiveness of repeated droplet passes to a conventional sink wash which used a wash bottle to squirt water and wash the sensor free of non-specific molecules. Evaluation of the two washing methods showed that a stationary HRP sample droplet left on the sensor for five minutes yielded a signal of 30 nA prior to washing. This signal should be considered the reference signal. The HRP molecules were non-specific for the sensor and did not bind significantly to it. Using the squirt bottle wash, the reference signal was reduced to a final signal value of 11 nA after repeated washing with water streams from the wash bottle. That is, about a 63% reduction of signal. Using a new HRP sample droplet and sensor, ten wash droplet passes were applied to the sensor thereby reducing the reference signal to a final signal value of 6 nA. That is about an 80% reduction. This demonstrates that repeated driving of wash droplets over the sensor is a more efficient way of washing the sensor than use of a conventional wash bottle.

The following claims are thus to be understood to include what is specifically illustrated and described above, what is conceptually equivalent, what can be obviously substituted and also what essentially incorporates the essential idea of the invention. Those skilled in the art will appreciate that various adaptations and modifications of the just-described preferred embodiment can be configured without departing from the scope of the invention. The illustrated embodiment has been set forth only for the purposes of example and that should not be taken as limiting the invention. Therefore, it is to be understood that, within the scope of the appended claims, the invention may be practiced other than as specifically described herein.

What is claimed is:

1. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor; and washing the sensing site by moving at least one droplet of a wash solution over the sensing site, wherein moving each discrete droplet comprises electrowetting.

2. The method according to claim 1, wherein the step of moving each droplet does not require valves, pumps or acoustic effects.

3. The method according to claim 1, wherein the target molecules are not denatured by the method.

4. The method according to claim 1, wherein a plurality of sensing sites are provided in parallel and a plurality of identical activities are undertaken simultaneously, one activity for each sensing site.

5. The method according to claim 4, wherein the activities at the plurality of parallel sensing sites improve statistical accuracy of detection of target molecules.

6. The method of claim 1, wherein moving each discrete droplet over a sensing site comprises transporting each discrete droplet to interact with each sensing site in a controlled manner.

7. The method of claim 1, further comprising moving droplets of wash to, and agitating over, sensor surfaces to remove non-target and unbound target molecules.

8. The method of claim 1, further comprising repeated driving of droplets of wash over the sensor.

9. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor; and moving at least one droplet of a substrate reaction solution or marker second antibody solution over the sensing site, wherein moving each discrete droplet comprises electrowetting.

10. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor; and agitating said droplet at the sensing site, wherein moving each discrete droplet comprises electrowetting.

11. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor; and concentrating said droplet at the sensing site by means of evaporation, wherein moving each discrete droplet comprises electrowetting.

12. The method according to claim 11, wherein the step of concentrating comprises creating a residual sessile droplet at the sensing site.

13. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor; and moving at least one droplet containing non-specific molecules over the sensing site to act as a reference for non-specific binding, wherein moving each discrete droplet comprises electrowetting.

14. The method of claim 1, A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, wherein each discrete droplet is comparable in size to the sensing site, and wherein moving each discrete droplet comprises electrowetting.

15. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, wherein moving each discrete droplet over a sensing site comprises moving each discrete droplet over the sensor in a plurality of directions, and wherein moving each discrete droplet further comprises electrowetting.

16. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, wherein moving each discrete droplet over a sensing site comprises holding the discrete droplet stationary over the sensor for a given time and moving the discrete droplet over the sensor at various velocities, and wherein moving each discrete droplet further comprises electrowetting.

17. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, wherein moving each discrete droplet over a sensing site comprises driving each discrete droplet over the sensor in a manner which produces localized agitation effects, and wherein moving each discrete droplet further comprises electrowetting.

18. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, wherein moving each discrete droplet over a sensing site comprises driving each discrete droplet over the sensor in a manner which brings particles in free suspension or molecules dissolved within the discrete droplet and/or residing on the liquid/air and liquid/surface interfaces of the discrete droplet into proximity to the sensor, and wherein moving each discrete droplet further comprises electrowetting.

19. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, wherein moving each discrete droplet over a sensing site comprises driving each discrete droplet over the sensor in a manner which mitigates adsorption of non-target molecules at the sensor site, and wherein moving each discrete droplet further comprises electrowetting.

20. A method for improving sensor detection of target molecules in a sample within a fluidic system comprising the steps of breaking the sample into a series of discrete droplets; moving each discrete droplet over a sensing site of a sensor thereby improving detection by furnishing multiple signals from the sensor, the method further comprising formation and evaporation of a sessile droplet, and wherein moving each discrete droplet comprises electrowetting.

* * * * *